United States Patent [19]

Mougin et al.

[11] Patent Number: 5,747,013
[45] Date of Patent: May 5, 1998

[54] MAKEUP COSMETIC COMPOSITION IN THE FORM OF A MASCARA CONTAINING AT LEAST A WAX AND A PSEUDO-LATEX OF CELLULOSE DERIVATIVES

[75] Inventors: Nathalie Mougin, Paris; Jean Mondet, Drancy; Bertrand Piot, La Garenne-Colombes; Alex Junino, Livry-Gargan; Jeanne Patraud, Paris, all of France

[73] Assignee: L'Oreal, Paris, France

[21] Appl. No.: 374,480

[22] Filed: Jan. 17, 1995

[30] Foreign Application Priority Data

Jan. 17, 1994 [FR] France .................. 94 00424

[51] Int. Cl.⁶ .................................. A61K 7/06
[52] U.S. Cl. .......................... 424/707; 424/401
[58] Field of Search ........................... 424/707, 401

[56] References Cited

U.S. PATENT DOCUMENTS

| | | | |
|---|---|---|---|
| 3,646,214 | 2/1972 | Katz | 424/302 |
| 4,536,405 | 8/1985 | Nara et al. | 514/781 |
| 4,988,502 | 1/1991 | Ounanian et al. | 424/63 |

FOREIGN PATENT DOCUMENTS 2400890  3/1979  France .

OTHER PUBLICATIONS

Harry's Cosmeticology by Ralph Harry, pp. 165–174, 1973.
JP–A–53 127 836 (Abstract).

*Primary Examiner*—Jyothsan Venkat
*Attorney, Agent, or Firm*—Nixon & Vanderhye, P.C.

[57] ABSTRACT

A mascara composition which comprises a mixture of:

(a) pseudo-latex particles, having an average diameter ranging from 10 to 300 nm, of a water-insoluble filmogen polymer derived form cellulose selected from the group consisting of cellulose ethers, non-ionic cellulose esters and anionic cellulose esters having carboxylic acid functions, the said carboxylic acid functions being neutralized to a neutralization amount between 10 and 80 percent by means of a nonvolatile basic agent, and (b) at least one wax having a melting point between 60° C. and 110° C.

13 Claims, No Drawings

MAKEUP COSMETIC COMPOSITION IN THE FORM OF A MASCARA CONTAINING AT LEAST A WAX AND A PSEUDO-LATEX OF CELLULOSE DERIVATIVES

The present invention relates to a cosmetic composition for makeup, principally the eyelashes and is designated a mascara composition, containing in combination, at least a wax and a pseudo-latex of cellulose derivatives.

A wax is currently employed to produce mascara compositions. However, wax is never employed alone because the makeup, with such compositions, turns out to be very mediocre conducting to the formation on the eyelashes of a nonhomogeneous film which shows by the formation of cracking pellicles, immediately after drying.

In order to remedy, it has been proposed in FR 83.09997 (2.528.699) and FR 84.17661 (2.573.305) the combined use of at least one wax and a filmogen polymer present in solution in the aqueous phase.

There have also been proposed, in WO/92/21316, treatment compositions for the treatment of hair and eyelashes containing a combination of a silicone, a latex and a suspension agent for the latex and silicone and/or a thickening agent.

Moreover, there have been proposed mascara compositions not containing wax. Thus, there has been described in JP 57-62216 (Kokai) an aqueous mascara composition containing, as a filmogen agent, synthetic latex.

If these compositions have permitted a certain improvement of the quality of the makeup products, they do not, however, provide a satisfactory lengthening of the eyelashes and are, moreover difficult to remove with water. It has now been ascertained, in a surprising and unexpected manner, that the combination of at least one wax and a pseudo-latex, particularly comprising particles of a polymer derived from cellulose, provides mascara compositions which significantly increase the lengthening and the bending of the eyelashes, and which are removable with water while having excellent cosmetic qualities.

It is recalled that the expression "pseudo-latex" designates a suspension constituted of generally spheric particles of a polymer which are obtained by dispersion of the polymer in an appropriate aqueous phase.

The expression "pseudo-latex" must not be confused with the expression "latex" or "synthetic latex" which is also a suspension constituted of particles of a polymer which are obtained directly by polymerization of one or several monomers in an appropriate aqueous phase.

More precisely, the present invention relates to a mascara composition containing in admixture, (a) a pseudo-latex constituted of particles having an average diameter between 10 and 300 nm, of a water-insoluble filmogen polymer derived of cellulose, and selected from cellulose ethers, nonionic cellulose esters and anionic cellulose esters having carboxylic acid functions, the said carboxylic acid functions being neutralized to a neutralization amount between 10 and 80 percent with a nonvolatile basic agent and
 (b) at least one wax having a melting point between 60° and 110° C., and, preferably, between 65° and 100°.

According to the invention, the mascara composition contains in admixture, 0.8 to 20 percent, and preferably from 1 to 10 percent of dry matter, of the pseudo-latex and 2 to 40 weight percent of at least one wax, these percentages being expressed relative to the total weight of the mascara composition.

According to the invention, the weight ratio between the pseudo-latex expressed by weight of dry matter and the wax is, preferably, between 0.025 and 2, and more particularly, between 0.5 and 1.

The average size of the particles of the pseudo-latex is preferably lower or equal to 250 nm.

The polydispersity in size of the particles is relatively weak and being measured in quasi-elastic light diffusion is generally between 0.05 and 0.40 and, preferably, lower than 0.35.

The weight concentration of the filmogen polymer under the form of particles in the pseudo-latex is generally between 5 and 50 percent and preferably between 10 and 25 percent relative to the total weight of the pseudo-latex.

The water-insoluble filmogen polymers derived from cellulose, such as defined above, have preferably an average molecular weight between 2,000 and 700,000, and in particular between 5,000 and 500,000, measured for example, by steric exclusion chromatography.

Among the cellulose ethers, insoluble in water, and useful as filmogen polymers according to the invention, mention can be made principally of ethylcelluloses and, in particular, those commercialized under the trade name "Ethocel" by Dow Chemical.

Among the nonionic cellulose esters which are insoluble in water and are useful as filmogen polymers according to the invention, mention can principally be made of cellulose acetates, cellulose propionates, cellulose butyrates, cellulose aceto-propionates and cellulose aceto-butyrates.

The pseudo-latex based on filmogen polymers as described above are obtained in accordance with known preparation methods of pseudo-latex.

The general preparation process of the pseudo-latex comprises dissolving the water-insoluble filmogen polymer in an organic solvent which is miscible or partially miscible in water, dispersing, under agitation, the solution thus obtained in the water at a temperature between ambient temperature and about 70° C., and evaporating under reduced pressure, and preferably under light heating, the organic solvent until its total removal. There is thus obtained a pseudo-latex, that is to say, an aqueous suspension of particles having, generally, a size lower than one μm.

The organic solvent employed must be a volatile solvent or a mixture of such solvents which exhibit a boiling point lower than that of water.

The organic solvent, such as defined above, is preferably selected from acetone, methylethylketone, tetrahydrofuran, 1,2-dichloroethane, methyl acetate, ethyl acetate, isopropanol and ethanol.

In accordance with this general process, there is preferably further employed a dispersing agent selected from a surface active agent, a mixture of surface active agents or a water-soluble colloidal protector polymer or also a surface active/water-soluble colloidal protector polymer mixture, with the view of improving the stabilization of the particles.

The useful surface-active agents employed in the present invention can be of the anionic, nonionic, cationic or amphoteric type. One preferably employs, however, surface-active agents of the anionic or nonionic type.

Among those mention can be made principally of sodium laurylsulfate.

Additionally, the employed surface-active agent can be combined with a costabilizer which is soluble in the organic phase such as cetyl alcohol.

As water-soluble colloid protector polymers, mention can principally be made of polyvinylalcohol, gum arabic and the polyoxyethylene/polyoxypropylene sequenced polymers.

When the insoluble in water filmogen polymer, derived from cellulose, is an anionic cellulose ester having carboxylic acid functions, it is selected among the following: cellulose acetophthalate, cellulose acetate succinate, cellulose propionate succinate, cellulose butyrate succinate, cellulose acetopropionate succinate, cellulose acetobutyrate succinate, cellulose acetate trimellitate, cellulose butyrate trimellitate, cellulose propionate trimellitate, cellulose acetopropionate trimellitate and cellulose acetobutyrate trimellitate.

The pseudo-latex constituted by the anionic cellulose esters, having carboxylic acid functions, are obtained in accordance with the general process, such as previously described, under reserve however of certain particularities.

The anionic cellulose esters having carboxylic acid functions, such as defined above, cannot be employed as such in the preparation of pseudo-latex but must be neutralized to a neutralization amount less than 100 percent so as to avoid their total water solubility.

By a partial neutralization of the polymers, it has been ascertained that it was possible to obtain pseudo-latex particularly stable in the absence of hydrophile stabilizing or surface-active agent or, even, colloid protector polymer.

The neutralization proportion of the filmogen polymers having carboxylic acid functions must, in addition, be perfectly determined so that they remain insoluble in water all while being soluble in the organic solvent.

It goes itself that the higher neutralization limit rate that will be suitable of not exceeding in order that the polymer remains, insoluble in water, will be function of the nature of each anionic cellulose ester having carboxylic acid functions. In a general manner, this neutralization amount is generally between 30 and 80 percent, and preferably between 40 and 70 percent, if the polymer has less than 2 meq/g of carboxylic acid functions and between 10 and 50 percent, preferably between 10 and 40 percent, if the polymer has more than 2 meq/g of carboxylic acid functions.

According to the present invention the neutralization of the carboxylic acid functions is realized with the aid of a nonvolatile basic agent selected, for example, among a mineral base such as soda or potash or among an amino alcohol selected in the group constituting of 2-amino-2-methyl-1-propanol (AMP), triethanolamine, triisopropanolamine (TIPA), monoethanolamine, diethanolamine, tri[(2-hydroxy)-1-propyl]amine, 2-amino-2-methyl-1,3-propanediol (AMPD) and 2-amino-2-hydroxymethyl-1,3-propanediol.

In the preparation of the pseudo-latex, employed in the compositions according to the invention, the neutralization of the carboxylic acid functions of the anionic cellulose ester is realized, in situ, in the solution of the polymer, in the organic solvent, by the addition of the determined amount of the nonvolatile basic compound.

The organic solvent used is such as defined previously in the general process.

After obtaining the solution of the anionic cellulose ester, partially neutralized in the organic solvent, the preparation of an emulsion is carried out by pouring under agitation, to the obtained organic solution, an appropriate amount of water eventually containing an anti-foam agent, the role of which will be to facilitate the subsequent evaporation of the organic phase.

According to a variation of the process, such as defined above, the neutralization of the carboxylic acid functions of the polymer in solution in the organic solvent can be realized during the formation of the emulsion by pouring an aqueous solution containing the requisite amount of the nonvolatile basic compound.

During the formation of the emulsion, the agitation is preferably realized employing a shearing disperser of the Moritz type, Ultra-Turrax or Raineri and equipped with deflocculant blades.

The emulsion thus obtained is particularly stable in the measure where the carboxylate groups of the polymer are placed at the interface with water and protect the droplets of the coalition by electrostatic repulsion.

After formation of the emulsion, elimination of the organic solvent is carried out under partial vacuum, such as previously described.

According to this mode of realization of the invention, a pseudo-latex is obtained which is free of any surface-active agent or other hydrophilic stabilizer and which is particularly stable.

There can be introduced in the pseudo-latex employed in the composition according to the invention, so as to improve its cosmetic and mechanical properties, a plasticizing agent in an amount between 5 and 90 percent and preferably between 10 and 80 percent by weight relative to the weight of the filmogen polymer, the said plasticizing agent, distributing according to its partition coefficient between the particles and the aqueous phase of the pseudo-latex.

The plasticizing agent which can be of the hydrophilic or hydrophobic type, is preferably introduced in admixture with the organic solvent during the preparation of the pseudo-latex, and principally when it is of the hydrophobic type.

When the plasticizing agent is of the hydrophilic type, it can be introduced after the formation of the pseudo-latex in the aqueous phase.

Among the plasticizing agents being able to be employed in the compositions according to the invention mention can be made of:

"Carbitols" of Union Carbide, namely "Carbitol" or diethylene glycol ethylether, "methyl Carbitol" or diethylene glycol methylether, "butyl Carbitol" or diethylene glycol butylether or "hexyl Carbitol" or diethylene glycol hexylether, "Cellosolves" of Union Carbide, namely "Cellosolve" or ethylene glycol ethylether, "butyl Cellosolve" or ethylene glycol butylether, "hexyl Cellosolve" or ethylene glycol hexylether, the propylene glycol derivatives and in particular, propylene glycol phenylether, propylene glycol diacetate, dipropylene glycol butylether, tripropylene glycol butylether, as well as the "Dowanols" of Dow Chemical, namely "Dowanol PM" or propylene glycol methylether, "Dowanol DPM" or dipropylene glycol methylether and "Dowanol TPM" or tripropylene glycol methylether.

Mention can also be made of:
the diethylene glycol methylether of "Dowanol DM" of Dow Chemical,
ricin oil oxyethylenated with 40 moles of ethylene oxide, such as that sold by Rhone Poulenc under the trade name "Mulgofen EL-719",
benzyl alcohol,
triethyl citrate sold by Pfizer under the trade name of "Citroflex-2",
1,3-butylene glycol,
diethyl, dibutyl and diisopropyl phthalates and adipates, diethyl and dibutyl tartarates,
diethyl, dibutyl and 2-diethyl-hexylphosphates and
glycerol esters such as glycerol diacetate (diacetin) and glycerol triacetate (triacetin).

Preferably employed is a plasticizing agent selected from the group consisting of dipropylene glycol methylether, tripropylene glycol methylether, diethyl adipate, diisopropyl adipate and glycerol triacetate.

The waxes employed in the mascara compositions according to the invention are selected from solid and rigid waxes of animal, vegetable, mineral or synthetic waxes and their mixtures.

The hardness of these waxes, measured by the penetration method of a needle, is generally between 3 and 40.

This method, described in the NFT 004 and ASTM D5 standards, French and American standards respectively, consists to measure, at a temperature of 25° C., the penetration depth, expressed in a millimeter tenth, of a normalized needle (weighing 2.5 g and placed in a port needle-carrier weighing 47.5 g, or to the total 50 g) placed on the wax for 5 seconds.

Among the animal waxes, mention can be made of beeswax, lanolin wax, and China insect waxes.

Among the vegetable waxes, mention can principally be made of rice wax, carnauba wax, candelilla wax, ouricurry wax, cork fiber wax, sugar cane wax, Japan wax and sumac wax.

Among the mineral waxes mention can principally be made of montan wax, microcrystalline waxes, paraffins and ozokerite.

Among the synthetic waxes, mention can be made of polyethylene waxes, waxes obtained by the Fisher and Tropsch synthesis and wax copolymers as well as their esters.

Also employable in the compositions according to the invention are waxes obtained by catalytic hydrogenation of animal or vegetable oils having linear or branched $C_8$–$C_{32}$ fatty chains.

Among these, mention can principally be made of hydrogenated jojoba oil, hydrogenated sunflower oil, hydrogenated ricin oil, hydrogenated copra oil and hydrogenated lanolin oil.

The viscosity of the mascara compositions, according to the present invention, expressed in deviation units and measured to contraves TV with a tool No. 4 for 10 minutes at 25° C., is generally between 21 and 85 deviation units and preferably between 25 and 64 deviation units.

The mascara compositions according to the present invention can, in addition, contain pigments.

These pigments can be organic or mineral or can also be nacre pigments. Such pigments are well known and are particularly described in FR 83.09997 (2.528.699).

The proportion of pigments, in the mascara compositions according to the invention, is generally between 3 and 25 weight percent relative to the total weight of the composition according to the coloration and intensity of the sought after coloration.

The mascara compositions, according to the invention, can be presented under different forms. They can, in particular, be presented under oil-in-water or water-in-oil emulsion form or under dispersion form.

In accordance with a preferred accomplishment form of the mascara compositions, according to the invention, they are presented under emulsion form containing at least an anionic or nonionic surface active agent in an amount between 2 and 30 weight percent relative to the total weight of the composition.

Among the anionic surface active agents which can be employed alone or in admixture, principal mention can be made of alkaline salts, ammonium salts, amine salts or amino-alcohol salts of the following compounds:

alkyl sulfates, alkylether sulfates, alkylamide sulfates, ether sulfates, alkylarylpolyether sulfates and monoglyceride sulfates, alkylsulfonates, alkylamide sulfonates, alkylaryl sulfonates, α-olefin sulfonates and paraffin sulfonates, alkylsulfosuccinates, alkylether sulfosuccinates and alkylamide sulfosuccinates, alkylsulfosuccinamates, alkylsulfoacetates and alkylpolyglycerol carboxylates, alkylphosphates/alkylether phosphates, alkylsarcosinates, alkylpolypeptidates, alkylamidopolypeptidates, alkylisethionates and alkyltaurates.

The term alkyl used above means a hydrocarbon chain having generally from 12 to 18 carbon atoms.

There can also be mentioned as anionic surface active agents, useful in the compositions according to the invention, fatty acid salts, such as those of oleic, ricinoleic, palmitic and stearic acid, copra oil or hydrogenated copra oil acids, and in particular, amine salts such as amine stearates.

There can also be mentioned, as anionic surface active agents, acyl lactylates the acyl radical of which contains 8 to 20 carbon atoms, and polyglycolic ether carboxylic acids having the formula

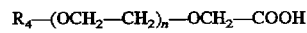

wherein $R_4$ represents a linear alkyl having 12 to 18 carbon atoms and n is a whole number between 5 and 15, and the salts of said acids. Preferably employed as the anionic surface active agent is amine stearates.

Among the nonionic surface active agents being able to be utilized, alone or in admixture, in the mascara compositions according to the invention, there can principally be mentioned alcohols, alkylphenols, and polyethoxylated, polypropoxylated or polyglycerolated fatty acids having a fatty chain from 8 to 18 carbon atoms.

There can also be mentioned copolymers of ethylene and propylene oxides, condensates of ethylene and propylene oxides on fatty alcohols, polyethoxylated fatty amides, polyethoxylated fatty amines, ethanolamides fatty acid esters of glycol, fatty acid esters of oxyethylene or non-oxyethylene sorbitan, fatty acid esters of saccharose, fatty acid esters of polyethylene glycols, phosphoric triesters and fatty acid ester derivatives of glucose.

Mention can also be made of the condensation products of a monoalcohol, an alpha-diol, an alkylphenol, an amide or a diglycolamide with glycidol or a glycidol precursor such as described in French patent, FR 71.17206 (2.091.516), having the formula

wherein $R_5$ represents an aliphatic, cycloaliphatic or arylaliphatic radical having, preferably, between 7 and 21 carbon atoms, the aliphatic chains optionally containing ether, thioether or hydroxymethylene groups, and p is a whole number between 1 and 10.

Further mention can be made of compounds, described in French patent 1.477.048, having the formula:

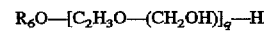

wherein $R_6$ represents an alkyl, alkenyl or alkylaryl radical and q has a statistical value between 1 and 10.

Mention can also be made of compounds described in French patent, FR 76.31975 (2.328.763) having the formula:

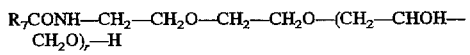

wherein $R_7$ represents a linear or branched, saturated or unsaturated, aliphatic, optionally containing one or several hydroxyl groups said aliphatic having between 8 and 30 carbon atoms, of natural or synthetic origin, and r is a, whole or decimal number between 1 and 5, and designates the average condensation degree.

Preferably there is employed, as the nonionic surface active agent, a mixture of oil(s) and/or fatty alcohols or even polyethoxylated or polyglycerolated alcohols, such as polyethoxyl stearyl or cetylstearyl alcohols.

The mascara compositions according to the present invention can also include at least a conventional additive selected from a softener, a preservative, a sequestering agent, a perfume, a thickening agent, an oil, a silicone, a cohesion agent, an alkalizing or acidifying agent, a water-soluble polymer and a charge.

The useful thickening agents in the mascara compositions according to the invention can be of natural or synthetic origin.

Among the thickening agents of natural origin,, there can principally be mentioned various gums, such as arabic, guar and carob gums.

Among the thickening agents of synthetic origin, mention can principally be made of water-soluble cellulosic derivatives, cellulose ether derivatives possessing quaternary ammonium groups, starch derivatives, cationic polysaccharides, acrylic or methacrylic polymer salts, polyenes and polysiloxanes.

In accordance with a preferred realized mode, the thickening agent of synthetic origin employed is a water-soluble cellulosic derivative selected from methylcelluloses, hydroxyethylcelluloses, hydroxypropylmethylcelluloses, carboxymethylcelluloses and their mixtures.

Mention can also be made for thickening the mascara compositions according to the invention by the addition of a mixture of a polyethylene glycol and polyethylene glycol stearate and/or distearate or a mixture of phosphoric esters and fatty amides.

Among the water-soluble polymers being able to be employed in the mascara compositions according to the invention, mention can principally be made of protein derivatives of animal or vegetable origin and, more particularly, keratin derivatives such as keratin hydrolyzates, and sulfonic keratins, polyvinylpyrrolidones, vinyl copolymers, such as the copolymer of methylvinyl ether and maleic anhydride or the copolymer of vinylacetate and crotonic acid, glycoaminoglycanes, hyaluronic acid and its derivatives and deoxyribonucleic acid and its salts.

Among the charges being able to be employed in the mascara compositions according to the present invention, mention can principally be made of those described in FR 91.10791 (2.680.681).

The following is an illustration of several preparation examples of the pseudo-latex, as well as mascara examples according to the present invention.

EXAMPLES OF PSEUDO-LATEX PREPARATION

Example I

Preparation of the pseudo-latex of cellulose acetobutyrate succinate polymer ("CAB SU 160" of Eastman) neutralized at 30% according to its acid index 30 g of the "CAB SU 160" polymer (succinate radicals content: 9 weight percent; acid index: 60) are added little by little under agitation to a homogeneous solution of 154.2 g of acetone, 0.858 g of 2-amino-2-methyl-1-propanol (amount corresponding to 30 percent of neutralization according to the acid index) and 15 g of diethyl adipate.

After agitation at ambient temperature for 30 minutes, the di-solution of the polymer is complete.

To the organic phase thus obtained, there is added in about 15 minutes, under agitation, using a shear disperser of the Moritz type at 2500 tr/min, an aqueous phase to produce an emulsion, which constitutes 154 g of permuted water.

After the end of the addition of the aqueous phase, at ambient temperature, the agitation is continued for 10 to 15 minutes at 3000 tr/min, which leads to the obtention of a translucid and stable emulsion.

The process then involves a concentration using a rotary evaporator under partial vacuum at a temperature lower than 45° C. After complete removal of the acetone, a stable suspension is obtained, the polymer concentration of which is 17 weight percent relative to the total weight of the dispersion.

The size of the particles has been measured in quasi-elastic light diffusion with Coulteur model M4 and has given the following results:

Average particle size: 101 nm
Polydispersity factor: 0.13

Example II

Preparation of the pseudo-latex of the ethylcellulose polymer ("Ethocel 10" of Dow Chemical) stabilized by a surface active agent 40 g of the "Ethocel 10" polymer are little by little added to a homogeneous solution of 759 g of 1,2-dichloroethane and 1 g of cetylalcohol. The combination of components is agitated using a shear disperser of the Moritz type at 3000 tr/min, at ambient temperature, until complete dissolution of the polymer, i.e. in about 30 minutes.

To the organic phase thus obtained, there is added in about 30 minutes, under agitation, an aqueous phase to achieve an emulsion which is constituted by 759 g of permuted water and 1 g of sodium laurylsulfate.

After the end of the addition of the aqueous phase, at ambient temperature, the agitation is continued for about 30 minutes, which leads to the obtention of a relatively coarse emulsion. The homogenization of the emulsion is proceeded using a high pressure homogenizer of the Soavib & Figli type, model OBL No. 2032, under a pressure of $75 \times 10^6$ Pa. After three passages, a fine and homogeneous emulsion is obtained.

The concentration is then achieved using a rotary evaporator under partial vacuum at a temperature lower or equal to 50° C. After complete removal of the 1,2-dichloroethane, a stable suspension, the polymer concentration of which is 20 weight percent relative to the total weight of the suspension, is obtained.

The size of the particles has been measured in quasi-elastic light diffusion with Coulteur model M4 and has given the following results:

Average particle size: 135 nm
Polydispersity factor: 0.09

Plasticizing of the above-obtained ethylcellulose pseudo-latex can also be achieved. To 200 g of the above-obtained suspension, there are added, little by little, 20 g of diethyl adipate under light magnetic agitation. A stable, fine homogeneous and slightly viscous suspension is obtained.

Example III

Preparation of the pseudo-latex of cellulose acetate ("AC 398-10" of Eastman) plasticized and stabilized by a surface-active agent 150 g of cellulose acetate "AC 398-10" are treated little by little under agitation in a homogeneous solution of 669 g of ethyl acetate, 1561 g of methylethylketone and 120 g of glycerol triacetate.

The above mixture is agitated at 3000 tr/min using a Moritz type disperser, at ambient temperature, until complete dissolution of the polymer, i.e. in about 30 minutes.

To the organic phase thus obtained, there is added in about 30 minutes, an aqueous phase to produce the emulsion, which is constituted of 7.5 g of sodium lauryl sulfate dissolved in 2903 g of permuted water.

After the end of the addition of aqueous phase, at ambient temperature, the agitation is continued for about 30 minutes at 3000 tr/min, which produces the production of a coarse emulsion.

The homogenization of the emulsion is carried out in accordance with the same procedure as described in Example II.

Then, the solution is concentrated using a rotary evaporator under partial vacuum at a temperature lower than 45° C. There is thus obtained a plasticized, stable and homogeneous pseudo-latex wherein the concentration of the dry extract relative to the total weight of the pseudo-latex is 14.2 percent by weight and wherein the concentration of the water-insoluble polymer derived from cellulose is 10.2 weight percent.

The size of the particles has been measured in quasi-elastic light diffusion with Coulteur model M4 and has given the following results:

Average particle size: 138 nm
Polydispersity factor: 0.10

EXAMPLES OF MASCARA

Example 1: Mascara cream

The following mascara composition has been prepared:

| Part A | |
|---|---|
| Triethanolamine stearate | 11.5 g |
| Beeswax | 7.0 g |
| Carnauba wax | 4.1 g |
| Paraffin | 11.4 g |
| Part B | |
| Black iron oxide | 5.5 g |
| Part C | |
| Gum arabic | 4.5 g |
| Hydroxyethylcellulose, sold under the tradename "Cellosize QP" by Amerchol | 0.16 g |
| Part D | |
| Pseudo-latex of Example I | 8.8 g |
| Preservatives, sufficient amount | |
| Water, sufficient amount for | 100 g |

This mascara is obtained by bringing the ingredients of part A to 85° C., to which part B is added and the mixture is agitated with a turbine mixer.

The water of the preparation, is then boiled, the preservatives are then added and at 85° C., the components of part C are added.

The aqueous phase obtained (85° C.) is added to part A (80° C.) under agitation using a centrifuge (emulsification at 30° C.) and the pseudo-latex of part D is finally added and agitated using a blade.

When the mascara thus obtained is employed by application onto the eyelashes, they appear longer and exhibit a pronounced curvature. Besides, the make-up removal can be easily accomplished with water.

Example 2: Mascara

In accordance with the same operative mode set forth in Example 1, a mascara having the following composition is prepared:

| Part A | |
|---|---|
| Triethanolamine stearate | 11.5 g |
| Beeswax | 7.0 g |
| Carnauba wax | 4.1 g |
| Paraffin | 11.4 g |
| Part B | |
| Black iron oxide | 5.0 g |
| Part C | |
| Gum arabic | 4.5 g |
| Hydroxyethylcellulose, commercialized under the trade name "Cellosize QP" by Amerchol | 0.16 g |
| Keratin hydrolysate, commercialized under the trade name "Kerasol" by Croda | 2.0 g |
| Part D | |
| Pseudo-latex of Example III | 14.1 g |
| Preservatives, sufficient amount | |
| Water, sufficient amount for | 100 g |

Example 3: Mascara

According to the same operative method as in Example 1, a mascara having the following composition is prepared:

| Part A | |
|---|---|
| Glyceryl stearate, commercialized under the trade name, "Geleol" by Gattefosse | 3.0 g |
| Triethanolamine stearate | 8.0 g |
| Beeswax | 7.0 g |
| Carnauba wax | 2.0 g |
| Paraffin | 10.0 g |
| Candelilla wax | 4.0 g |
| Part B | |
| Coal black | 2.5 g |
| Part C | |
| Gum arabic | 4.5 g |
| Hydroxyethylcellulose, commercialized under the trade name "Cellosize QP" by Amerchol | 0.2 g |
| Part D | |
| Pseudo-latex of Example II | 12.5 g |
| Preservatives, sufficient amount | |
| Water, sufficient amount for | 100 g |

We claim:

1. A mascara composition in the form of an oil-in-water or water-in-oil emulsion or dispersion comprising a mixture of:

(a) a particle suspension of a water-insoluble filmogen polymer in an aqueous phase, said particles having an average diameter ranging from 10 to 300 and said water-insoluble filmogen polymer being selected from the group consisting of ethylcelluloses, cellulose acetates, cellulose propionates, cellulose acetobutyrates and anionic cellulose esters having carboxylic acid functions, the said carboxylic acid functions being neutralized to a neutralization amount of between 10 and 80 percent by means of a non-volatile basic agent, and (b) at least one wax having a melting point between 60° C. and 110° C.

2. The mascara composition of claim 1 wherein said wax has a melting point between 65° C. and 100° C.

3. The mascara composition of claim 1 which contains from 0.8 to 20 percent by weight of dry material of the particle suspension and 2 to 40 weight percent of at least a wax based on the total weight of the said composition.

4. The mascara composition of claim 1 wherein the weight ratio between the particle suspension expressed in weight of dry material and the wax is between 0.025 and 2.

5. The mascara composition of claim 1 wherein said filmogen polymer has an average molecular weight between 2,000 and 700,000.

6. The mascara composition of claim 1 wherein said filmogen polymer has an average molecular weight between 5,000 and 500,000.

7. A mascara composition in the form of an oil-in-water or water-in-oil emulsion or dispersion comprising a mixture of:

(a) a particle suspension of a water-insoluble filmogen polymer in an aqueous phase, said particles having an average diameter ranging from 10 to 300 nm and wherein said filmogen polymer is an anionic cellulose ester having carboxylic acid functions selected from the group consisting of cellulose acetophthalate, cellulose acetate succinate, cellulose propionate succinate, cellulose butyrate succinate, cellulose acetopropionate succinate, cellulose acetobutyrate succinate, cellulose acetate trimellitate, cellulose propionate trimellitate, cellulose butyrate trimellitate, cellulose acetopropionate trimellitate and cellulose acetobutyrate trimellitate, the said carboxylic acid functions being neutralized to a neutralization amount of between 10 and 80 percent by means of a non-volatile basic agent, and (b) at least one wax having a melting point between 60° C. and 110° C.

8. The mascara composition of claim 7 wherein the carboxylic acid functions of the anionic cellulose ester are neutralized with a non-volatile basic agent selected from the group consisting of soda, potash, 2-amino-2-methyl-1-propanol, triethanolamine, triisopropanolamine, monoethanolamine, diethanolamine, tri amine, 2-amino-2-methyl-1,3-propanediol and 2-amino-2-hydroxymethyl-1,3-propanediol.

9. The mascara composition of claim 1 wherein the said particle suspension contains a plasticizing agent in an amount between 5 and 90 weight percent relative to the weight of the filmogen polymer, the said plasticizing agent being distributed according to its position coefficient between the particles and the aqueous phase of the particle suspension.

10. The mascara composition of claim 1 wherein the said wax is selected from the group consisting of beeswax, lanolin wax, China insect wax, rice wax, carnauba wax, candelilla wax, ouricurry wax, cork fiber wax, sugar cane wax, Japan wax, sumac wax, montan wax, microcrystalline waxes, paraffins, ozokerite, polyethylene waxes and hydrogenated oils.

11. The mascara composition of claim 1 also containing a pigment in an amount between 3 and 25 percent by weight relative to the total weight of the composition.

12. The mascara composition of claim 1 which is present in the form of an emulsion containing at least an anionic or nonionic surface active agent in an amount between 2 and 30 weight percent relative to the total weight of said composition.

13. The mascara composition of claim 1 containing at least a conventional additive selected from the group consisting of a softening agent, a preservative, a sequestering agent, a perfume, a thickening agent, an oil, a silicone, a cohesion agent, an alkalizing or acidifying agent, a water-soluble polymer and a charge.

\* \* \* \* \*